United States Patent
Wort et al.

(10) Patent No.: US 8,193,538 B2
(45) Date of Patent: Jun. 5, 2012

(54) ELECTRONIC FIELD EFFECT DEVICES

(75) Inventors: Christopher John Howard Wort, Berkshire (GB); Geoffrey Alan Scarsbrook, Berkshire (GB); Ian Friel, Berkshire (GB); Richard Stuart Balmer, Berkshire (GB)

(73) Assignee: Diamond Microwave Devices Limited (GB)

( * ) Notice: Subject to any disclaimer, the term of this patent is extended or adjusted under 35 U.S.C. 154(b) by 197 days.

(21) Appl. No.: 12/523,960

(22) PCT Filed: Jan. 22, 2008

(86) PCT No.: PCT/IB2008/050216
§ 371 (c)(1),
(2), (4) Date: Sep. 3, 2009

(87) PCT Pub. No.: WO2008/090512
PCT Pub. Date: Jul. 31, 2008

(65) Prior Publication Data
US 2010/0078651 A1    Apr. 1, 2010

(30) Foreign Application Priority Data

| Jan. 22, 2007 | (GB) | 0701186.9 |
| Mar. 22, 2007 | (GB) | 0705523.9 |
| Mar. 22, 2007 | (GB) | 0705524.7 |
| May 21, 2007 | (GB) | 0709716.5 |
| Jul. 11, 2007 | (GB) | 0713464.6 |

(51) Int. Cl.
*H01L 29/15* (2006.01)

(52) U.S. Cl. .................. 257/77; 257/213; 257/E21.041

(58) Field of Classification Search .................. 257/77, 257/213, E21.041, E29.002
See application file for complete search history.

(56) References Cited

U.S. PATENT DOCUMENTS

| 5,276,338 A * | 1/1994 | Beyer et al. ................. 257/52 |
| 5,491,348 A | 2/1996 | Koyamao et al. |
| 5,506,422 A | 4/1996 | Dreifus et al. |
| 5,609,926 A | 3/1997 | Prins et al. |
| 5,803,967 A * | 9/1998 | Plano et al. ................. 117/102 |
| 6,177,292 B1 | 1/2001 | Hong et al. |
| 6,207,282 B1 | 3/2001 | Deguchi et al. |
| 2004/0256624 A1 | 12/2004 | Sung |
| 2005/0109262 A1 | 5/2005 | Linares et al. |

(Continued)

FOREIGN PATENT DOCUMENTS
EP    0343963 A2    11/1989
(Continued)

OTHER PUBLICATIONS

Ariki et al., "Efficient field effect in heavily doped thin-film diamond metal-insulator-semiconductor diode employing BaTiO3 insulator film", Japanese Journal of Applied Physics, vol. 33, pp. L888-L891 (1994).

(Continued)

*Primary Examiner* — Kiesha Bryant
*Assistant Examiner* — Tucker Wright
(74) *Attorney, Agent, or Firm* — Bryan Cave LLP

(57) ABSTRACT

Electronic field effect devices, and methods of manufacture of these electronic field effect devices are disclosed. In particular, there is disclosed an electronic field effect device which has improved electrical properties due to the formation of a highly mobile two-dimensional charge-carrier gas in a simple structure formed from diamond in combination with polar materials.

8 Claims, 6 Drawing Sheets

U.S. PATENT DOCUMENTS

| | | | |
|---|---|---|---|
| 2005/0127373 | A1 | 6/2005 | Yokota et al. |
| 2008/0121897 | A1* | 5/2008 | LaRoche et al. ............... 257/77 |

FOREIGN PATENT DOCUMENTS

| | | | |
|---|---|---|---|
| EP | 0458530 | A2 | 11/1991 |
| EP | 0496564 | A1 | 7/1992 |
| EP | 0697738 | A1 | 2/1996 |
| EP | 0741118 | A2 | 11/1996 |
| EP | 0994074 | A2 | 4/2000 |
| EP | 1536043 | A1 | 7/2005 |
| EP | 1555337 | A2 | 7/2005 |
| EP | 1571241 | A1 | 9/2005 |
| EP | 1712661 | A1 | 10/2006 |
| GB | 2281254 | A | 3/1995 |
| GB | 2358409 | A | 7/2001 |
| GB | 2252202 | A | 7/2002 |
| GB | 2428690 | A | 2/2007 |
| JP | 60246627 | A | 12/1985 |
| JP | 2002 057167 | A | 2/2002 |
| JP | 2006 216716 | A | 8/2006 |
| WO | 99 22049 | A1 | 5/1999 |
| WO | 01 75197 | A1 | 10/2001 |
| WO | 01 96633 | A1 | 12/2001 |
| WO | 01 96634 | A1 | 12/2001 |
| WO | 03 014427 | A1 | 2/2003 |
| WO | 03 052174 | A2 | 6/2003 |
| WO | 2004 027123 | A1 | 4/2004 |
| WO | 2005 074013 | A2 | 8/2005 |
| WO | 2006 013430 | A1 | 2/2006 |
| WO | 2006 061707 | A2 | 6/2006 |
| WO | 2006 117621 | A1 | 11/2006 |
| WO | 2007 066215 | A2 | 6/2007 |

OTHER PUBLICATIONS

Choi et al., "Properties of natural diamond microlenses fabricated by plasma etching," Industrial Diamond Review, Issue 2, 2005, pp. 29-31.

Choi et al., "Fabrication and Evaluation of GaN Negative Bifocal Microlenses," Journal of Applied Physics, 97 (2005), 063101-1-063101-3.

Choi et al., Fabrication of natural diamond microlenses by plasma etching, J. Vac. Sci. Technol. B, 23 (2005), 130-132.

Crisman et al., "Large pyroelectric response from reactively sputtered aluminum nitride thin films," Electrochemical and Solid-State Letters, 8, 2005, pp. H31-H32.

Denisenko et al., "Diamond power devices. Concepts and Limits," Diamond and Related Materials, vol. 14, No. 3-7, pp. 491-498.

Enlund et al., "Anisotropic dry etching of boron doped single crystal CVD diamond," Carbon, 43, pp. 1839-1842.

"Ion Backscattering Analysis," in Concise Encylopedia of Material Characterization, R.W. Cahn and E. Lifshin, eds., Pergamon (London), 1993, pp. 199-204.

Karlsson et al., "Transfer of continuous-relief diffractive structure into diamond by use of inductively coupled plasma dry etching," Optics Letters, 26, 2001, pp. 1752-1754 (p. 215-217).

Karlsson et al., "Transfer of micro-optical structures into GaAs and diamond," Proceedings of the SPIE, vol. 4561, 2001, pp. 114-122.

Koide, Y., "Analysis for Electron Concentrations in n-diamond/III-nitride heterostructure and phosphorus delta-doped structure in diamond", Japanese Journal of Applied Physics, vol. 44, 2005, pp. 55-59.

Koide, Y., "Enhancement of donor ioinization in phosphorus-doped n-diamond", Applied Surface Science, col. 244, pp. 26-29 (2205).

Kondo et al., "Homoepitaxial single-crystal boron-doped diamond electrodes for electroanalysis," Journal of the Electrochemical Society, vol. 149, No. 6, Jun. 2002, pp. E179-E184.

Kondo et al., "Plasma etching treatment for surface modification of boron-dopied diamond electrodes," Electrochimica Acta, 52, 2007, 3841-3842.

Lee, et al., "Fabrication and characterization of diamond micro-optics," Diamond and Related Materials 15, 2006, pp. 725-728.

Miskys C. et al., "AlN/diamond heterojunction diodes", Applied Physics Letters, vol. 82, pp. 290-292 (2003).

Miskys C. R. et al., "Structural and interface properties of an AlN diamond ultraviolet light emitting diode", Applied Physics Letters, vol. 83, pp. 3699-3701 (2004).

Nebel C. et al., "AlN/diamond np-junctions," Diamond and Related Materials, 12, 2003, pp. 1873-1876.

Okumura, H., "Present status and future prospect of widegap semi-conductor high-power devices," Japanese Journal of Applied Physics, 45, 2006, 7565-7586.

Pearton "ECR plasma etching of chemically vapour deposited diamond thin films," Electronics Letters, Apr. 1992, pp. 822-824.

Samlenski et al., "Characterisation and lattice location of nitrogen and boron in homoepitaxial CVD diamond," Diamond and Related Materials, vol. 5, No. 9, Jul. 1996, pp. 947-951.

Sine et al., "Electrochemical behavior of fluorinated boron-doped diamond," Electrochemical and Solid-State Letters, 6, 2003, D9-11.

Tavares et al., "{111}-oriented diamond films and p/n junctions grown on B-doped type lb substrates," Diamond and Related Materials, vol. 14, No. 3-7, Mar. 2005, pp. 522-525.

Vogg et al., "High quality heteroepitaxial AlN films on diamond," Journal of Applied Physics, 96, 2004, 895-902.

International Search Report for PCT/IB200/050214 dated May 27, 2008.

International Search Report for PCT/IB200/050215 dated May 28, 2008.

International Search Report for PCT/IB200/050216 dated May 27, 2008.

International Search Report for PCT/IB200/050218 dated Jun. 13, 2008.

International Search Report for PCT/IB200/050219 dated Jun. 16, 2009.

UK Search Report for GB0709716.5 dated Sep. 21, 2007.
UK Search Report for GB0701186.9 dated Jul. 5, 2007.
UK Search Report for GB0705524.7 dated Jul. 16, 2007.
UK Search Report for GB0713464.6 dated Oct. 26, 2007.
UK Search Report for GB0705523.9 dated Jul. 20, 2007.
A.R. Lang, "The Properties of Diamond," Chapter 14 "Internal Structure," Ed. J.E. Field, Academic Press London 1979, p. 434.

* cited by examiner

ELECTRONIC FIELD EFFECT DEVICES

FIELD OF THE INVENTION

The present invention relates to electronic field effect devices, and to methods of manufacture of these electronic field effect devices.

BACKGROUND OF THE INVENTION

The present generation of high frequency (HF) and microwave signals is now mostly based on Si and GaAs devices. Due to physical limitations, these devices cannot achieve power levels higher than a few hundred watts (depending on the frequency to be amplified) in simple solid-state device configurations. Wide band gap materials (diamond, SiC, GaN, etc), in principle, allow for higher power amplification per unit gate length at microwave frequencies. This is because a larger bias voltage, and hence the voltage amplitude on the microwave signal, can be supported across the transistor channel region over which the current is modulated. In effect, the higher breakdown electric field of a wide band gap semiconductor is exploited. In microwave transistors, the ability to support high voltage is particularly desirable since, generally, power has to be transferred to a relatively high impedance (50 $\Omega$) load.

The use of diamond in manufacturing transistors of various types has been described in, for example, JP-A-60246627, EP 0 343 963 B1 and WO 2006/117621 A1.

WO 2006/117621 A1 discloses a metal semiconductor field-effect transistor (MESFET). The MESFET is manufactured by providing a single crystal diamond material substrate having a growth surface on which further layers of diamond material can be deposited, depositing a plurality of further diamond layers on the substrate growth surface, and attaching appropriate contacts to the respective diamond layers, thereby defining a transistor structure. The further diamond layers deposited on the substrate include a boron doped interface layer (a "delta-doped" layer). Such a design presents several synthesis challenges. The main challenge is the requirement to produce nanometer-thin boron layers which transition very abruptly to an intrinsic layer (e.g. a change in B concentration from about $10^{15}$ B atoms per cm$^3$ to about $10^{20}$ B atoms per cm$^3$ in a few nm). Growing such boron layers (delta layers) is dependent upon a number of crucial steps including substrate surface preparation and diamond growth conditions. In addition to the synthesis challenges, certain aspects of the device design are not ideal. In particular, the holes (acting as charge carriers) are essentially localised in the vicinity of the acceptors, which leads to an increase in impurity scattering and an overall degradation in the mobility.

U.S. Pat. No. 5,506,422 discloses a diamond-based three-terminal junction device that uses a material with a wider band gap than diamond to enhance the blocking properties of the gate contact. The disclosure states that conduction from the source to the drain is confined to a boron-doped layer. The use of the wide band gap material in the gate contact is not fundamental to the operation of the device, but simply a means of enhancing its performance by reducing leakage under reverse bias. By using the boron-doped layer as the channel the device of U.S. Pat. No. 5,506,422 does not exploit the superior charge carrier properties of intrinsic diamond compared with boron doped diamond.

Vogg et al (Journal of Applied Physics, vol 96 (2004), 895-902) and Nebel et al (Diamond and Related Materials, vol 12 (2003), 1873-1876) disclose pn junction diodes made from {100} and {111} diamond with an epitaxial layer of aluminium nitride. For both orientations of diamond substrate surface, it is reported in Vogg et al that there is a significant lattice parameter mismatch (−13% and +23% for {100} and {111} respectively), and that the AlN layers have a domain structure. Nebel et al reports, "The leakage current in the reverse direction is caused by imperfections of the pn heterojunction, probably caused by dislocations". The carrier path of the device described is across the interface from the p-type doped diamond layer to the n-type doped AlN layer. This suggests that the structure of the interface between the diamond substrate and the AlN layer is highly defective, something that would be extremely detrimental to performance of an electronic device where charge flows across the interface.

Accordingly, it is an object of the invention to provide an alternative device structure, and a method of manufacture thereof, having particular advantages in terms of device manufacture and performance. Another object of the invention is to provide an alternative device structure and a method of manufacture thereof in which the charge carriers and any ionised acceptors/donors are spatially separated.

In III-V systems such as GaAs and GaN, spatial separation of the charge carriers and ionised acceptors or donors can be achieved by modulation doping. This is facilitated by the ability to form heterostructures through alloying, i.e. the addition of one or more group III or V elements into the matrix such as In or Al to change the energy band-gap of the material, whilst retaining essentially the same crystal structure across the interface. In silicon, a group IV element, heterostructures can be formed by alloying Si with Ge, another group IV element. Alloying of diamond with Si would form SiC. As SiC has a smaller band gap than diamond, such a heterostructure formed with diamond would lead to charge carrier confinement within the SiC layer and the superior electronic properties of the diamond would not be exploited.

A heterostructure is characterised by a lattice match (that is essentially the same lattice type, essentially the same lattice orientation and with a lattice parameter that is closely matched between the two materials) across the interface of the two distinct materials, and in normal usage typically refers to the situation where there is lattice continuity and the interface is defined by a distinct change in the relative concentrations of alloy components. This does not exclude the possibility of a small difference in the lattice parameter from which could give rise to an array of "misfit dislocations" at the interface. A related concept is that of heteroepitaxial growth, where the lattices on the two sides of the boundary may be distinct, but at the interface there is a substantial match or registration between the lattices.

The publication 'Present Status and Future Prospect of Widegap Semiconductor High-Power Devices', Japanese Journal of Applied Physics, 45 (2006), 7565-7586 provides a useful summary of prior art. FIG. 6 of the publication discloses a GaN—Al$_x$Ga$_{(1-x)}$N heterostructure in which a polar Al$_x$Ga$_{(1-x)}$N layer is heteroepitaxially grown on a polar GaN layer to produce a potential well for confining electrons.

SUMMARY OF THE INVENTION

The present invention provides an electronic field effect device comprising:
 an interface between two materials, wherein the interface is formed by:
  a first diamond layer, at least a first surface of which comprises crystalline intrinsic diamond, and
  a second layer disposed on the first surface of the first layer, wherein the second layer is polar; wherein there is a discontinuity in polarisation between the first layer and the second layer; and there is a band offset between the first layer and the second layer, in the band in which the dominant charge carriers are present, such that the dominant charge carriers are confined to a planar region within the first layer and in close proximity to the interface by the combined effects of a polarization induced sheet charge and an electric field provided by the discontinuity in polarization between the first layer and the second layer, and the band offset.

The dominant charge carriers provide the useful characteristics of the device.

The planar region comprises a region having two dimensions which are very much larger than the third.

The charge carriers in the device under operation are confined to the planar region in the first diamond layer and move predominantly in a direction parallel to the interface between the first layer and the second layer. Therefore any defects such as dislocations that are present in the second layer adjacent to the interface have little effect on the performance of the device.

The electric field provided by the discontinuity in polarization between the second layer and the first layer attracts the carriers towards the polar material and thus the interface.

The dominant carriers may be present in either the valence band or the conduction band.

The band offset inhibits the carriers from entering the polar material.

At least one of the first layer and the second layer may include a doped region. The doped region then provides carriers which can move to and subsequently be confined to the planar region.

In a preferred embodiment, instead of doping either of the first and second layers, the electric field provided by the discontinuity in polarization between the second layer and the first layer may cause the valence band maximum to intersect the Fermi level. In such a case, holes are generated at the interface which act as carriers which can move to and subsequently be confined to the planar region. In such a case, the 2-dimensional charge carrier gas is formed from thermally generated carriers and no dopant is required in either the first layer or the second layer.

Alternatively, instead of doping either of the first and second layers, the electric field provided by the discontinuity in polarization between the second layer and the first layer may cause the conduction band minimum to intersect the Fermi level. In such a case, electrons are generated at the interface which act as carriers which can move to and subsequently be confined to the planar region. In such a case, the 2-dimensional charge carrier gas is formed form thermally generated carriers and no dopant is required in either the first layer or the second layer.

When a dopant is present in the first layer, it preferably resides in a layer which is further away from the interface than the planar region, and sufficiently remote from the planar region to avoid the dopant significantly impeding the mobility of the carriers and thus degrading the device performance. Thus the doped region in the first layer is preferably at least 2 nm from the interface, more preferably at least 3 nm from the interface, more preferably at least 5 nm from the interface, more preferably at least 10 nm from the interface, more preferably at least 20 nm from the interface, more preferably at least 50 nm from the interface, and more preferably at least 100 nm from the interface. The distance between the interface and the doped region may be influenced by the dopant concentration in the doped layer to ensure the correct number density of charge carriers in the 2-dimensional charge carrier gas, where the meaning of the term "2-dimensional charge carrier gas" is as is normally understood in the art.

In a preferred embodiment, the first layer comprises an intrinsic diamond layer including a doped region positioned a distance from the interface such that the polar layer and the doped region are separated by an intrinsic diamond channel layer. The doped region in the intrinsic diamond may comprise an n-type region or a p-type region. When the doped region comprises a p-type region, the charge carriers are holes. The p-type doped region may comprise a boron-doped region. When the doped region comprises an n-type region, the charge carriers are electrons. The n-type doped region may comprise a nitrogen-doped region or a phosphorus-doped region.

Unlike the MESFET disclosed in WO 2006/117621 A1, the doped layer does not have to be a delta-layer and does not have to be atomically abrupt with respect to the intrinsic diamond channel. Preferably, the square modulus of the wave function of the charge carriers ($|\phi(z)|^2$) does not overlap with the doped layer, but resides mostly within the intrinsic layer. The thicknesses of each of the layers of the device may be limited by the requirement that the doped layer must be capable of being fully depleted by the gate so that the transistor can be operated in pinch-off mode.

The doped region is preferably prepared by the technique of in-situ doping (that is doping during the crystal growth process). In particular, the doped region is preferably prepared in the first diamond layer by in-situ doping, preferably using boron atoms as the dopant species.

Alternatively, the doped region may be prepared by the technique of ion implantation. In particular, the doped region may be prepared in the first diamond layer by ion implantation, preferably of boron ions or atoms.

At the interface, the two layers may be in direct contact such that there is no other material interposed. Alternatively, a thin interface material may be provided between the two layers. Preferably such an interface material forms a layer which is less than 5 nm thick, more preferably less than 2 nm thick, more preferably less than 1 nm thick. The interface material may be between 0.1 nm and 5 nm thick. The interface material may be a different material to both the first and second layers. The interface material may be amorphous or crystalline in nature. Preferably the interface material is a non-rigid, compliant material. The interface material may be atomic hydrogen. Such a layer may be formed by hydrogenation. Preferably the interface material is an insulating material. An example of an interface layer might be 0.5 nm of amorphous silicon dioxide ($SiO_2$). The interface material may be provided in order to passivate or accommodate dangling bonds at the interface. Such dangling bonds may trap charge carriers, increase charge carrier scattering, and/or reduce mobility and conductivity.

The first diamond layer is a wide band-gap semiconducting material, preferably non-polar, more preferably single crystal diamond, more preferably single crystal CVD diamond, and more preferably single crystal CVD diamond with material properties conforming to the disclosures in WO 01/96633 and WO 01/96634.

The second layer preferably has a wider bandgap than the first layer, and more preferably comprises MN in its wurtzite phase. An alternative second layer may comprise $Al_xGa_{(1-x)}N$ where $x \geq 0.8$.

Since there are two types of charge carrier possible in such a device, electrons and holes, then the device can take two distinct forms.

In the case where the dominant charge carrier type is holes, the holes are confined to the planar region by the combined effects of a polarization field provided by the polar layer, and a valence band offset between the first and second layers, wherein the polarization field has a polarization vector which points away from the interface and which leads to the attraction of the holes towards the interface, and the valence band offset forms a potential energy barrier inhibiting holes from entering the polar layer, wherein the valence band maximum of the second layer is less than the valence band maximum of the first layer.

In the case where the dominant charge carrier type is electrons, the electrons are confined to the planar region by the combined effects of a polarization field provided by the polar layer, and a conduction band offset between the first and second layers, wherein the polarization field has a polarization vector which points towards the interface and which leads to the attraction of the electrons towards the interface, and the conduction band offset forms a potential energy barrier inhibiting electrons from entering the polar layer, wherein the conduction band minimum of the second layer is greater than the conduction band minimum of the first layer.

In a preferred embodiment of the invention, the band gap of the second layer is larger than that of the first layer.

In a further preferred embodiment, the band gap of the second layer is larger than that of the first layer, and the band offset in the conduction band and valence band is such that both electrons and holes are inhibited from entering the polar material, that is the valence band maximum of the second layer is less than the valence band maximum of the first layer and the conduction band minimum of the second layer is greater than the conduction band minimum of the first layer. This situation is known as a "type I band offset".

When the dominant carriers are holes, the valence band offset moving from the first layer to the second layer is negative and its modulus is preferably greater than 0.05 eV, more preferably greater than 0.1 eV, more preferably greater than 0.15 eV, more preferably greater than 0.2 eV, more preferably greater than 0.3 eV, more preferably greater than 0.4 eV, and more preferably greater than 0.5 eV.

In principle, there is no upper limit to the modulus (or largest negative value) of the applicable valence band offset, provided that the device is suitably designed such that the holes are retained in an intrinsic region of the first layer. There is a practical limit in the current availability of materials, of about 2 eV, but this is not limiting on the scope of the present invention.

When the dominant carriers are electrons, the conduction band offset moving from the first layer to the second layer is positive and preferably greater than +0.05 eV, more preferably greater than +0.1 eV, more preferably greater than +0.15 eV, more preferably greater than +0.2 eV, more preferably greater than +0.3 eV, more preferably greater than +0.4 eV, and more preferably greater than +0.5 eV.

In principle, there is no upper limit to the modulus (or largest positive value) of the applicable conduction band offset, provided that the device is suitably designed such that the electrons are retained in an intrinsic region of the first layer. There is a practical limit in the current availability of materials, of about 2 eV, but this is not limiting on the scope of the present invention.

When the bandgap of the second layer is larger than the bandgap of the first layer, then it is preferably larger by 0.1 eV, more preferably larger by 0.2 eV, more preferably larger by 0.3 eV, more preferably larger by 0.4 eV, more preferably larger by 0.6 eV, more preferably larger by 0.8 eV, more preferably larger by 1.0 eV, and more preferably larger by 1.2 eV. For the purposes of the present invention, the bandgap of diamond is taken to be 5.47 eV.

In principle, there is no upper limit to the bandgap of the second layer, provided that the device is suitably designed such that the carriers are retained in an intrinsic region of the first layer. There is a practical limit in the current availability of materials, of about 9 eV, but this is not limiting on the scope of the present invention.

The device may comprise a three-terminal device. Preferably, the device comprises a field-effect transistor (FET). In view of the fact that in this device the polar layer leads to the spatial separation and confinement of the charge carriers in the planar region which leads to an enhancement in the performance of the device, the device shall be termed herein a "Polarization Enhanced-FET" or PE-FET. The PE-FET may comprise appropriate electric contacts in order to define the transistor structure. The electrical contacts may comprise a gate, a source and a drain.

Discontinuity in polarisation between the non-polar intrinsic diamond layer and the polar second layer creates a polarisation-induced sheet charge $\sigma_p = -(P_n)$ at the interface between the two layers where $P_n$ is the component of polarisation in the polar layer normal to the interface between the two layers. $P_n$ is defined as positive when it points away from the interface between the two layers. Such a sheet charge leads to a significant strength electric field in both the diamond layer and the second polar layer. The sheet charge is not mobile because it is a manifestation of the atomic dipoles in the polar second layer, which are fixed by the polar material's crystal structure. The band offset acts as a potential barrier. This potential barrier, coupled with the electric field results in a triangular potential well which can be used to attract carriers, resulting in a highly confined two-dimensional electron gas or hole gas in the region of the diamond layer close to the interface.

The extent of the confined two-dimensional charge carrier gas defines the region referred to as the planar region. This region is not necessarily flat over large dimensions, e.g. over dimensions larger than 1 μm, more preferably larger than 10 μm, more preferably larger than 100 μm, more preferably larger than 1 mm, but will conform to any large scale curvature of the interface between the first and second layer. Sharp features in the interface between the first and second layer, which would result in relatively sharp features in the planar region, are not desirable and may degrade the performance of the device by causing scattering of the charge carriers. This is controlled by careful preparation of the surfaces forming the interface between the first and second layer. In particular, the first surface of the first layer preferably has root-mean-square roughness $R_q$ of less than 10 nm, preferably an $R_q$ of less than 5 nm, preferably an $R_q$ of less than 3 nm, preferably an $R_q$ of less than 2 nm, preferably an $R_q$ of less than 1 nm, preferably an $R_q$ of less than 0.5 nm preferably an $R_q$ of less than 0.3 nm, preferably an $R_q$ of less than 0.2 inn, preferably an $R_q$ of less than 0.1 nm. Furthermore, the surface of the second layer facing the first layer preferably has an $R_q$ of less than 10 nm, preferably an $R_q$ of less than 5 nm, preferably an $R_q$ of less than 3 nm, preferably an $R_q$ of less than 2 nm, preferably an $R_q$ of less than 1 nm, preferably an $R_q$ of less than 0.5 nm, preferably an $R_q$ of less than 0.3 nm, preferably an $R_q$ of less than 0.2 nm, preferably an $R_q$ of less than 0.1 nm.

It is desirable that the first layer has a low dislocation density in the region of the first surface. In particular, it is desirable that the density of dislocations breaking the first surface of the first layer is less than 400 $cm^{-2}$, preferably less than 300 $cm^{-2}$, preferably less than 200 $cm^{-2}$, preferably less than 100 $cm^{-2}$, measured over an area of greater than 0.014 cm², preferably greater than 0.1 cm², preferably greater than 0.25 cm², preferably greater than 0.5 cm², preferably greater than 1 cm², and preferably greater than 2 cm².

Methods of preparing and characterising diamond and diamond surfaces with low dislocation density are reported in the prior art of WO 01/96633, WO 01/96634, WO 2004/027123, and co-pending application PCT/IB2006/003531. The preferred methods of characterising the dislocation density are the use of a 'revealing plasma etch' and the use of x-ray topography.

It is further desirable that the surface of the first layer is substantially free from damage introduced by post-growth mechanical processing of the as-grown surface to a depth of at least 1 nm, preferably at least 2 nm, preferably at least 5 nm, preferably at least 10 nm, preferably at least 20 nm, preferably at least 50 nm, preferably at least 100 nm, preferably at least 200 nm, preferably at least 500 nm. The presence of such damage, which includes microfractures and mechanically-generated point and extended defects, can have a detrimental effect on the performance of a device through carrier scattering and trapping, perturbation of the local electric field and degradation of the breakdown electric field.

In the case of diamond and in particular single crystal CVD diamond, such defects can be introduced into the material by mechanical processing of the as-grown surface, such as by using conventional lapping and polishing techniques. These issues are particularly relevant to diamond in view of its hard and brittle nature, and its chemical resistivity which limits the number of chemical and physical etching processes available. The requirements for processing an electronic surface for low roughness, and those for processing an electronic surface for low surface damage are quite distinct. The preparation of an electronic surface showing both these features is a further aspect of this invention.

Generally, thick layers of single crystal CVD diamond in the as-grown state are not suitable for use as the first layer and their surfaces are not suitable for use as the first surface because of the presence of non-planar features that can develop during growth. Conversely, the diamond layer on which the electronic surface is to be prepared needs to be sufficiently rigid and robust for processing and handling, and consequently the fabrication of an electronic device usually starts from a thick diamond layer. There are a number of methods of producing a suitable diamond surface from the as-grown surface of a thick diamond layer, which processing steps are included in the method. In the context of this invention, a single crystal CVD layer is considered to be thick when its thickness exceeds 20 µm.

Firstly, a surface may be prepared on the thick diamond layer using mechanical lapping and polishing processes, which have been optimised for minimum surface damage by using feedback from, for example, a revealing etch. Such a technique is described in for example WO 01/96633 and WO 01/96634. Whilst such a surface may have a low damage level, it is unlikely to be sufficiently free of damage to obtain more than adequate performance from the device.

The first surface may be prepared from a processed surface, preferably from a mechanically processed surface, preferably a mechanically prepared surface itself optimised for minimum surface damage by using the method above, by using a further processing stage comprising chemical etch or other forms of etching, such as ion beam milling, plasma etching or laser ablation, and more preferably plasma etching. Preferably the etching stage removes at least 10 nm, preferably at least 100 nm, more preferably at least 1 µm, more preferably at least 2 µm, more preferably at least 5 µm, more preferably at least 10 µm. Preferably the etching stage removes less than 100 µm, preferably less than 50 µm, preferably less than 20 µm. This further processed surface preferably has an $R_q$ of less than 10 nm, preferably an $R_q$ of less than 5 nm, preferably an $R_q$ of less than 3 nm, preferably an $R_q$ of less than 2 nm, preferably an $R_q$ of less than 1 nm, preferably an $R_q$ of less than 0.5 nm preferably an $R_q$ of less than 0.3 nm, preferably an $R_q$ of less than 0.2 nm, preferably an $R_q$ of less than 0.1 nm.

Alternatively, the first surface may be prepared from a processed surface, preferably from a mechanically processed surface, preferably a mechanically prepared surface itself optimised for minimum surface damage by using the method above, or from an etched surface such as those described above, by growing a further thin layer of diamond on the surface, preferably using a CVD process. Prior to deposition of the further thin layer of diamond, the processed surface has an $R_q$ of less than 10 nm, preferably an $R_q$ of less than 5 nm, preferably an $R_q$ of less than 3 nm, preferably an $R_q$ of less than 2 nm, preferably an $R_q$ of less than 1 nm, preferably an $R_q$ of less than 0.5 nm preferably an $R_q$ of less than 0.3 nm, preferably an $R_q$ of less than 0.2 nm, preferably an $R_q$ of less than 0.1 nm.

Such a diamond layer is preferably grown by CVD synthesis, and is thin to limit the formation of macroscopic growth steps. The thickness of this layer, grown onto a previously prepared surface, is less than 20 µm, preferably less than 10 µm, preferably less than 1 µm, preferably less than 100 nm, preferably less than 50 nm, preferably less than 20 nm, preferably less than 10 nm. The surface of this thin layer is then used as the first surface in its as grown state.

Such a thin layer may be prepared using a number of techniques including monolayer growth techniques and use of off-axis surfaces to control the propagation of surface steps.

The surface preferably has Miller indices close to those of a {001} surface, as this is a surface upon which homoepitaxial CVD diamond growth is most easily accomplished. Alternatively the surface may have Miller indices close to those of a {111} surface, as such a surface has been found to be the most suitable for the deposition of AlN layers. The normal to the surface is preferably between 0° and about 5°, preferably between about 0.5° and about 1°, of the normal to a {001} or a {111} surface. Where the surface is close to a {001} surface, the normal to the surface is preferably within about 10° of the great circle passing through the pole of the {001} surface and the pole of an adjacent {101} surface.

Such a layer preferably comprises high purity intrinsic diamond, more preferably high purity intrinsic diamond with material properties conforming to the disclosures in WO 01/96633 and WO 01/96634

The surface of this thin as-grown layer forms the first surface and preferably has an $R_q$ of less than 10 nm, preferably an $R_q$ of less than 5 nm, preferably an $R_q$ of less than 3 nm, preferably an $R_q$ of less than 2 nm, preferably an $R_q$ of less than 1 nm, preferably an $R_q$ of less than 0.5 nm preferably an $R_q$ of less than 0.3 nm, preferably an $R_q$ of less than 0.2 nm, preferably an $R_q$ of less than 0.1 nm. Thus, this surface has very low surface roughness and in addition is free of processing damage.

In the case of diamond, the prepared surface onto which this layer may be grown could be any form of diamond, but is preferably CVD synthetic diamond, and where the first layer contains a doped layer, more preferably CVD synthetic diamond with the doped layer already present, more preferably this doped layer already formed by CVD synthesis.

The doped layer may form the surface which is processed prior to the final synthesis of the intrinsic semiconductor layer.

The polar layer may comprise a pyroelectric material or a piezoelectric material. However, the primary source of the polar field is from the pyroelectric properties of the polar layer, even if a piezoelectric effect is also present. The polar layer may comprise AlN which has a band gap energy, $E_g$=6.2 eV, and which would provide an electric field strength of significantly greater than 1 MVcm$^{-1}$ at the interface between the diamond and AlN layers. AlN offers the advantages of having a wide band gap, being commercially readily available, and having a large spontaneous polarisation and good thermal properties as well as robustness.

The polar second layer may comprise a composite layer formed of two or more polar layers. Forming such a composite polar second layer provides an alternative method for controlling the density of the two-dimensional carrier gas more accurately. The polar layers are preferably III-V polar materials such as AlN or Al$_x$GaN. For example, the second layer may comprise a composite layer comprising an AlN layer with an Al$_x$GaN layer formed thereon.

For a material to be a polar layer in its unstressed state, the crystallographic point group should be one of the following: 1, 2, m, mm2, 3, 3 m, 4, 4 mm, 6 or 6 mm, where the notation is the Hermann-Mauguin notation. The preferred material AlN has point group 6 mm.

Alternatively, a material having one of the piezoelectric crystallographic point groups that is not polar could be made polar by depositing it in a stressed state. The relevant piezoelectric crystallographic point groups are, in the Hermann-Mauguin notation: 222, $\bar{4}$, 422, $\bar{4}2$ m, 32, $\bar{6}$, 622, and $\bar{6}2$ m.

The direction of the polarization vector P of a polar material is a property of its crystal structure. Using aluminium nitride as an example, the [0001] crystallographic direction is parallel to one set of Al—N bonds and is defined as being from the Al atom to the N atom. The Al atom is charged slightly positive and the nitrogen is charged slightly negative, and, due to spatial arrangement of the atoms a spontaneous polarisation P is formed. In AlN P is always in the [000$\bar{1}$] direction.

The identification of candidate materials for the polar layer that meet the necessary criteria on the band offsets and band gap is not trivial, particularly when the first layer is already such a wide band gap material as diamond. Possible candidate materials include:

SiO$_2$ in the form of quartz (point group 32) in the stressed state, and hexagonal boron nitride (point group 6 mm).

The present invention also provides a method of forming an electronic field-effect device comprising:

forming an interface between a first layer and a second layer by:
  providing a first diamond layer, at least a first surface of which comprises crystalline intrinsic diamond; and
  providing a second layer, wherein the second layer is polar, and the second layer is arranged on the first surface of the first layer, wherein:
there is a discontinuity in polarisation between the first layer and the second layer; and
there is a band offset between the first layer and the second layer, in the band in which the dominant charge carriers are present, such that the dominant charge carriers are confined to a planar region within the first layer and in close proximity to the interface by the combined effects of a polarization induced sheet charge and an electric field provided by the discontinuity in polarisation between the first layer and the second layer, and the band offset.

Although conceptually the device comprises a first and second layer, this does not restrict the order of fabrication. For example, the second layer may be formed on a pre-existing first layer, for example by PVD or CVD processes, or the first layer may be formed on a pre-existing second layer, for example by PVD or CVD processes, or the two layers may be formed completely separately and then bonded together.

The conventional methods of charge carrier confinement used in other systems, such as heterostructures and modulation doping, are impractical in diamond. Thus, despite substantial interest in developing devices which exploit the extreme electronic properties of diamond, all effort has focused on controlled structures within the diamond, such as doped delta layers, because alternative options taught by the prior art in other semiconductor systems are not applicable to diamond. However, the method of this invention provides for forming a highly mobile 2D gas of carriers in diamond, using simple diamond structures in combination with other, polar materials.

A particular issue with diamond is that of surface termination. It is well known that the electron affinity of diamond can be modified with respect to that of a clean diamond surface by terminating the diamond surface with hydrogen or oxygen for instance. Since the position of the band offsets between two dissimilar materials can be a function of the electron affinities of those materials (known in the art as "Anderson's Rule"), the use of a suitably terminated diamond surface could be used to control the band offsets in such a way as to improve device performance by controlling such parameters as the 2D gas density and the spatial profile of the carrier wave functions. For example, the electron affinity is believed to be decreased for a hydrogen terminated surface compared with an unterminated surface. Thus, whilst an ideal structure may go directly from a first diamond layer to a second polar layer, for example AlN, in reality this interface may contain a fractional monolayer, a monolayer or multiple monolayers of other chemical species such as H, O, F, OH (including the various isotopic alternatives of each of these) etc. It may be desirable to deliberately terminate the diamond layer with a non-carbon species, or in other ways insert such species at the interface, in order to control the conduction and valence band offsets between the diamond layer and the polar layer. This technique is particularly relevant since there is no requirement for lattice continuity across the interface. As previously mentioned, an amorphous or atomic hydrogen layer may be provided at the interface layer to passivate any dangling bonds. Such an atomic hydrogen layer may be provided by hydrogenation.

Where a surface has a specific surface termination, the surface may be terminated such that the proportion of bonds on the surface with the specific surface termination is preferably about 60% or more, preferably about 70% or more, preferably about 80% or more, preferably about 90% or more.

The first layer may comprise natural diamond or synthetic diamond. Synthetic diamond used in the present invention may be formed by a high-pressure-high-temperature (HPHT) process or more preferably by chemical vapour deposition (CVD). If the CVD diamond layer is single crystal, then preferably the polar layer, such as AlN is bonded to the CVD diamond layer, or more preferably formed on the CVD diamond layer. Where the CVD diamond layer is polycrystalline, it would be preferable, in some instances, to form the polycrystalline CVD diamond layer onto the polar layer.

The polar layer may be formed on the diamond layer by deposition, for example growth by CVD (e.g. MOCVD or MOVPE) or molecular beam epitaxy (MBE). Alternatively, the polar layer may be attached to the diamond layer by bonding. Since the polar layer must not only be capable of showing polarity, but must also provide a polarization-induced electric field at the interface between the first and second layers, the polar layer cannot be amorphous or polycrystalline with randomly oriented polar domains. Preferably, the polar layer comprises polar domains of good crystalline quality which are substantially aligned in the desired direction to provide at the interface a relatively uniform polarization-induced electric field of the required magnitude and orientation. The most preferred form in this respect would be a single crystal polar material. However, well-oriented polycrystalline material is suitable. Significant variation in the polarization-induced electric field provided at the diamond surface, and in particular variations caused by local inversion domains in the polar layer, would provide a scattering mechanism for the carriers and degrade the performance of the device. For the example of AlN, either the [0001] or [000$\bar{1}$] direction (depending upon whether the device uses holes or electrons as the charge carrier) of AlN is preferably normal to the intrinsic diamond surface in order to align and maximize $\sigma_P$, but a combination of significant domains of both orientations is highly undesirable.

An advantage of bonding the polar layer to the intrinsic diamond layer is that good quality material of single polarity is readily available. The polar layer may have good quality crystal structure. However, there is no need to lattice match the polar layer to the intrinsic diamond layer. The means of bonding must not impact substantially on the device performance. However, the bonding medium may form the additional interface layer separating the first and second layers as described earlier. A technique that may be used to bond the polar layer to an intrinsic diamond layer is anodic bonding.

In a preferred embodiment, the intrinsic diamond layer includes a doped region. The intrinsic diamond layer may include a doped layer positioned a distance from the interface such that the polar layer and the doped layer are separated by an intrinsic diamond channel layer and the doped layer is arranged between the intrinsic diamond channel layer and an intrinsic diamond substrate layer.

The doped layer in the intrinsic diamond may comprise an n-type layer or a p-type layer. When the doped layer comprises a p-type layer, the charge carriers are holes. The p-type doped layer may comprise a B-doped layer. When the doped layer comprises an n-type layer, the charge carriers are electrons. The n-type doped layer may comprise a nitrogen-doped layer or a phosphorus-doped layer. The doped layer may be prepared by implantation, for example implanting B ions, or preferably it is prepared by CVD synthesis, for example adding gases such as diborane to the synthesis process. CVD synthesis of the doped layer may take place in situ with the other layers, or it may take place in a separate synthesis stage to the intrinsic diamond, particularly the intrinsic diamond layer forming the first surface in which the charge carriers for the 2 dimensional carrier gas.

When the doped region is a p-type region in the intrinsic diamond layer (i.e. holes are used as carriers), the polar layer is arranged so that a component of its polarisation vector P points away from the interface between the intrinsic diamond and the polar layer (i.e. towards the surface of the device). For example, where the polar layer comprises AlN, N-polar AlN is used. The polarisation sheet charge formed at the interface will then be negative and will consequently attract the holes as charge carriers towards the polar layer. The valence band offset between the polar layer and the intrinsic diamond layer may be chosen so that the holes are prevented from entering the polar layer. The valence band offset acts as a potential barrier. This potential barrier coupled with the attractive force leads to an approximately triangular potential well in which a two-dimensional hole gas (2DHG) is formed. The hole wave function is a maximum in the intrinsic diamond channel layer. Therefore, the 2DHG is localised in the intrinsic diamond channel close to the interface between the intrinsic diamond channel and the polar layer. Since the 2DHG is formed in the intrinsic diamond channel layer, rather than along the interface, the carriers are spatially separated from the ionised acceptors and the holes have a very high mobility.

When the doped region is an n-type region in the intrinsic diamond layer, the polar layer is arranged so that a component of its polarisation vector P points towards the interface between the intrinsic diamond and the polar layer (i.e. away from the surface of the device). For example, where the polar layer comprises AlN, Al-polar AlN is used. The polarisation sheet charge formed at the interface will then be positive and will consequently attract the electrons as charge carriers towards the polar layer. The conduction band offset between the polar layer and the intrinsic diamond layer may be chosen so that the electrons are prevented from entering the polar layer. The conduction band offset acts as a potential barrier. This potential barrier coupled with the attractive force leads to a triangular potential well in which a two-dimensional electron gas (2DEG) is formed. The electron wave function is a maximum in the intrinsic diamond channel layer. Therefore, the 2DEG is localised in the intrinsic diamond channel close to the interface between the intrinsic diamond channel and the polar layer. Since the 2DEG is formed in the intrinsic diamond channel layer, rather than along the interface, the carriers are spatially separated from the ionised donors and the electrons have a very high mobility. Furthermore, performance is further improved because electrons have a higher mobility in diamond than holes.

In another preferred embodiment, the polar layer includes the doped region. The entire polar layer may be doped or part of the polar layer may be doped, this part preferably forming a plane substantially parallel to the interface between the first and second layers. Consequently the device may comprise a doped polar layer or an undoped/doped/undoped stack arranged on a first surface of an intrinsic diamond layer. With this embodiment, the diamond synthesis is less demanding because only a high quality intrinsic diamond layer is required. This is achievable in volume production. Furthermore, there is no potential problem of incomplete depletion of a doped region within the intrinsic diamond layer, which would prevent the transistor operating in pinch-off mode.

The doped polar layer may comprise an n-type layer or a p-type layer. When the doped polar layer comprises a p-type layer, the charge carriers are holes. The doped polar layer may comprise $Al_xGa_{1-x}N$ doped with Mg (where $x \geq 0.8$ to ensure $E_g > 5.47$ eV). When the doped layer comprises an n-type layer, the charge carriers are electrons. Electrons as charge carriers are preferred because they have a higher mobility than holes. The doped polar layer may comprise AlN doped with Si. Alternatively, the doped polar layer may comprise $Al_xGa_{1-x}N$ doped with Si (where $x \geq 0.8$ to ensure $E_g > 5.47$ eV). A further advantage of using AlN or $Al_xGa_{1-x}N$ (where $x \geq 0.8$) as the polar layer is that the relative dielectric constant of these materials is very much greater than diamond (>10 compared to 5.7 for diamond). From Gauss' law, the product of the relative dielectric constant ($\in_r$) and the normal electric field of two materials has to be constant at their interface. Therefore, during operation the peak electric field should be in the intrinsic diamond layer rather than the AlN (or $Al_xGa_{1-x}N$) layer. This is advantageous because the breakdown field strength of diamond is significantly greater than that of most other materials (10 $MVcm^{-1}$), so there will be an associated improvement in the device breakdown voltage (and therefore operating voltage range) enabling a higher peak output power compared to alternative device configurations.

When the doped polar layer is an n-type layer, the polar layer is arranged so that a component of its polarisation vector P points towards the interface between the intrinsic diamond and the polar layer (away from the surface of the device). The polarisation sheet charge formed at the interface will then be positive and will consequently result in charge transfer of electrons from the polar layer into the intrinsic diamond layer. The conduction band offset between the polar layer and the intrinsic diamond layer acts as a potential barrier. This potential barrier coupled with the attractive force leads to an approximately triangular potential well in which a two-dimensional electron gas (2DEG) is formed. The electron wave function is a maximum in the intrinsic diamond layer. Therefore, the 2DEG is localised in the intrinsic diamond layer close to the interface between the intrinsic diamond layer and the polar layer. Since the 2DEG is formed in the intrinsic diamond layer, the carriers are spatially separated from the ionised donors and the electrons have a very high mobility.

When AlN doped with Si is used as the doped polar layer, even though the donor activation energy in AlN is very large compared to typical operating temperatures, the >1 MV cm$^{-1}$ strength electric field in the AlN layer will ensure field-assisted tunnelling of electrons into the diamond layer. If $Al_xGa_{1-x}N$ doped with Si is used as the doped polar layer (with x chosen to ensure the potential well in the intrinsic diamond layer is maintained), a higher concentration of Si donors could be incorporated, and a higher proportion of the donors could be ionised. However, $Al_xGa_{1-x}N$ used as the polar layer instead of AlN would lead to a reduced electric field strength and potentially lead to a lower band offset, which may in combination lead to a lower 2DEG density.

When the doped layer is a p-type layer, the polar layer is arranged so that a component of its polarisation vector P points away from the interface between the intrinsic diamond layer and the polar layer (towards the surface of the device). The polarisation sheet charge formed at the interface will then be negative and will consequently result in charge transfer of holes from the polar layer into the intrinsic diamond layer. The valence band offset between the polar layer and the intrinsic diamond layer acts as a potential barrier. This potential barrier coupled with the attractive force leads to a triangular potential well in which a two-dimensional hole gas (2DHG) is formed. The hole wave function is a maximum in the intrinsic diamond layer. Therefore, the 2DHG is localised in the intrinsic diamond layer close to the interface between the intrinsic diamond layer and the polar layer. Since the 2DHG is formed in the intrinsic diamond layer, the carriers are spatially separated from the ionised acceptors and the holes have a very high mobility.

In addition to doping the first or second layer to provide charge carriers, the first and/or the second layer may be further doped in order to provide opposite charges that modify the polarisation induced electric field and alter the two-dimensional carrier gas density.

In another preferred embodiment, neither the intrinsic diamond layer nor the polar layer includes a doped region.

The polar layer may be arranged so that a component of its polarisation vector P points away from the interface between the intrinsic diamond and the polar layer (i.e. towards the surface of the device). The electric field provided by the discontinuity in polarization between the second layer and the first layer causes the valence band maximum to intersect the Fermi level. Holes would be generated near the interface which act as carriers. For example, where the polar layer comprises AlN, N-polar AlN is used. The polarisation sheet charge formed at the interface will then be negative and will consequently attract the holes as charge carriers towards the polar layer. The valence band offset between the polar layer and the intrinsic diamond layer would be chosen so that the holes are prevented from entering the polar layer. The valence band offset acts as a potential barrier. This potential barrier coupled with the attractive force leads to an approximately triangular potential well in which a two-dimensional hole gas (2DHG) is formed. The hole wave function is a maximum in the intrinsic diamond channel layer. Therefore, the 2DHG is localised in the intrinsic diamond channel close to the interface between the intrinsic diamond channel and the polar layer.

Alternatively, the polar layer may be arranged so that a component of its polarisation vector P points towards the interface between the intrinsic diamond and the polar layer (i.e. away from the surface of the device). The electric field provided by the discontinuity in polarization between the second layer and the first layer causes the conduction band minimum to intersect the Fermi level. Electrons would be generated near the interface which act as carriers. For example, where the polar layer comprises AlN, Al-polar AlN is used. The polarisation sheet charge formed at the interface will then be positive and will consequently attract the electrons as charge carriers towards the polar layer. The conduction band offset between the polar layer and the intrinsic diamond layer may be chosen so that the electrons are prevented from entering the polar layer. The conduction band offset acts as a potential barrier. This potential barrier coupled with the attractive force leads to a triangular potential well in which a two-dimensional electron gas (2DEG) is formed. The electron wave function is a maximum in the intrinsic diamond channel layer. Therefore, the 2DEG is localised in the intrinsic diamond channel close to the interface between the intrinsic diamond channel and the polar layer. Furthermore, performance is further improved because electrons have a higher mobility in diamond than holes.

BRIEF DESCRIPTION OF THE DRAWINGS

Embodiments of the present invention will now be described with reference to the following drawings in which.

DETAILED DESCRIPTION OF THE DRAWINGS

Figure 1:
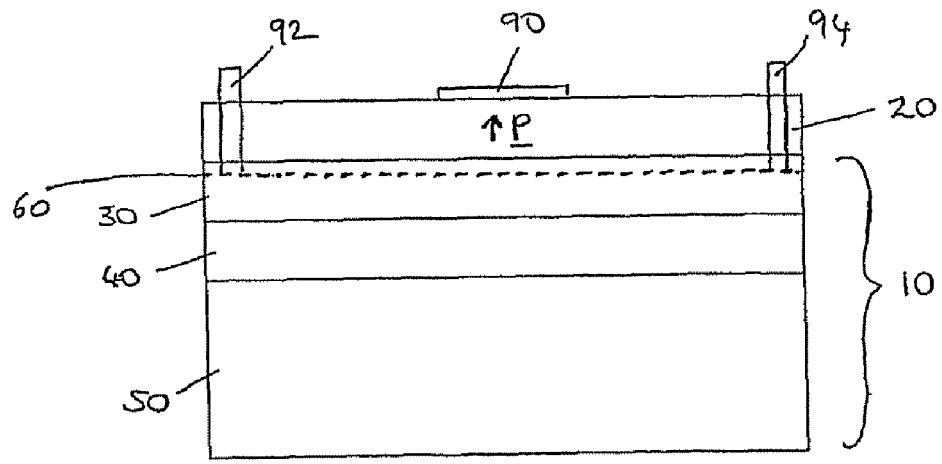
FIG. 1 shows a first embodiment of a FET according to the present invention.

A first embodiment of the present invention is shown in FIG. 1. A polar layer 20 is disposed on an intrinsic diamond layer 10 so that its polarisation vector points substantially away from the interface between the polar layer 20 and the intrinsic diamond layer 10. The polar layer is either grown or bonded onto the intrinsic diamond layer. The polar layer 20 has a band gap greater than that of the intrinsic diamond layer 10. The intrinsic diamond layer has a band gap, $E_g$, of 5.47 eV. The polar layer may comprise an N-polar AlN layer with a band gap of 6.2 eV. The intrinsic diamond layer 10 includes a B-doped layer 40 of thickness t positioned a distance d from the interface between the intrinsic diamond layer 10 and the polar layer 20. Thickness t and distance d are chosen such that the doped layer can be fully depleted by the gate 90 and pinch-off can be achieved. The B-doped layer splits the intrinsic diamond layer into an intrinsic diamond channel 30 and an intrinsic diamond substrate 50. A gate contact 90 is arranged on the polar layer 20 and a source 92 and a drain 94 are arranged to contact the intrinsic diamond channel 30.

With an N-polar AlN layer, the discontinuity in polarisation between the intrinsic diamond layer 10 and the polar layer 20 creates a negative polarisation sheet charge $-\sigma_P$ at the interface between the two layers. This sheet charge leads to a significant strength electric field. For an AlN layer as the polar layer, the electric field strength in the intrinsic diamond channel 30 is estimated to be about 8 MVcm$^{-1}$.

Figure 2:
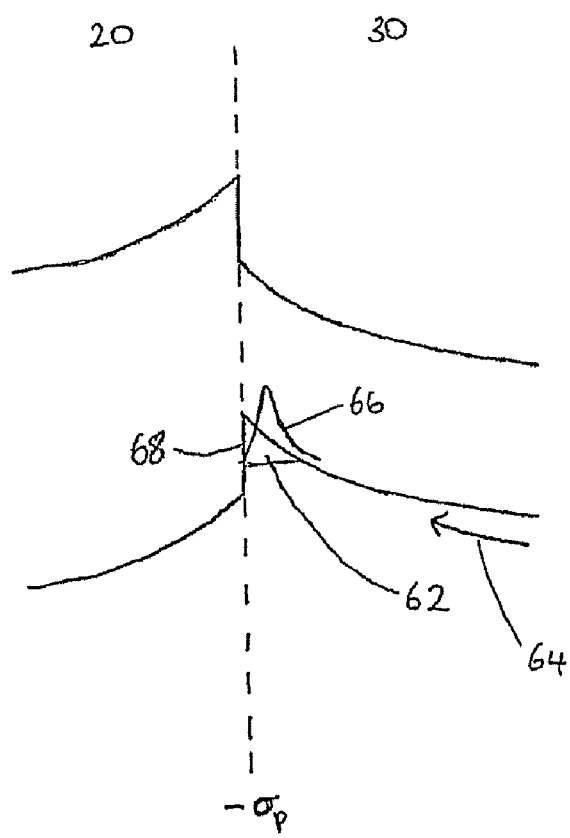
FIG. 2 shows an energy band diagram for the interface between the polar and diamond layers shown in FIG. 1.

An energy band diagram for the interface between the polar layer and the intrinsic diamond channel is shown in FIG. 2.

The B-doped layer 40 acts as a source of holes and the electric field resulting from the polarisation sheet charge $-\sigma_P$ attracts the holes from the B-doped layer 40 towards the interface with the polar layer 20, along path 64 as shown in FIG. 2. The discontinuity 68 in the valence band maxima between the diamond layer 10 and the polar layer 20 acts as a potential barrier which prevents transfer of holes from the diamond layer into the polar layer. The holes 62 are trapped in a triangular potential well in the intrinsic diamond channel close to the interface with the polar layer. This results in a highly confined 2DHG in region 60 of the intrinsic diamond channel close to the interface.

The square modulus of the hole wave function $|\phi(z)|^2$ 66 is a maximum in the diamond layer, rather than at the interface. Therefore, transport of holes occurs in the high purity and high crystalline quality intrinsic diamond channel rather than along the doped region or the polar layer or along the interface itself, any of which would lead to significant carrier scattering effects.

Figure 3:
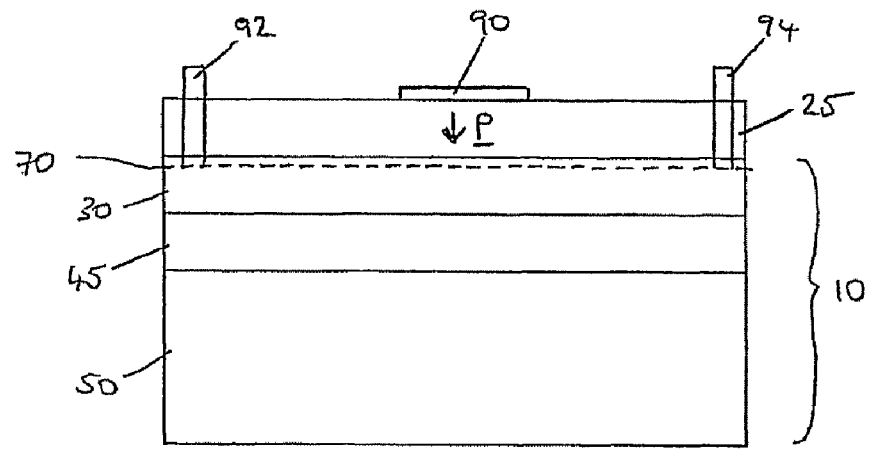
FIG. 3 shows a second embodiment of a PEFET according to the present invention.

A second embodiment of the present invention is shown in FIG. 3. A polar layer 25 is disposed on an intrinsic diamond layer 10 so that its polarisation vector points substantially towards the interface between the polar layer 25 and the intrinsic diamond layer 10. The polar layer is either grown or bonded onto the intrinsic diamond layer. The polar layer 25 has a band gap greater than that of the intrinsic diamond layer 10. The intrinsic diamond layer has a band gap, $E_g$, of 5.47 eV. The polar layer may comprise an Al-polar AlN layer with a band gap of 6.2 eV. The intrinsic diamond layer 10 includes an n-type doped layer 45, such as phosphorus or nitrogen, of thickness t positioned a distance d from the interface between the intrinsic diamond layer 10 and the polar layer 20. Thickness t and distance d are chosen so that the doped layer can be fully depleted by the gate 90 and pinch-off can be achieved. The n-type doped layer 45 splits the intrinsic diamond layer 10 into an intrinsic diamond channel 30 and an intrinsic diamond substrate 50. A gate contact 90 is arranged on the polar layer 25 and a source 92 and a drain 94 are arranged to contact the intrinsic diamond channel 30.

With an Al-polar AlN layer, the discontinuity in polarisation between the intrinsic diamond layer 10 and the polar layer 25 creates a positive polarisation sheet charge $+\sigma_P$ at the interface between the two layers. This sheet charge leads to a significant strength electric field. For an AlN layer as the polar layer, the electric field strength in the intrinsic diamond channel 30 is estimated to be about 8 MVcm$^{-1}$.

Figure 4:
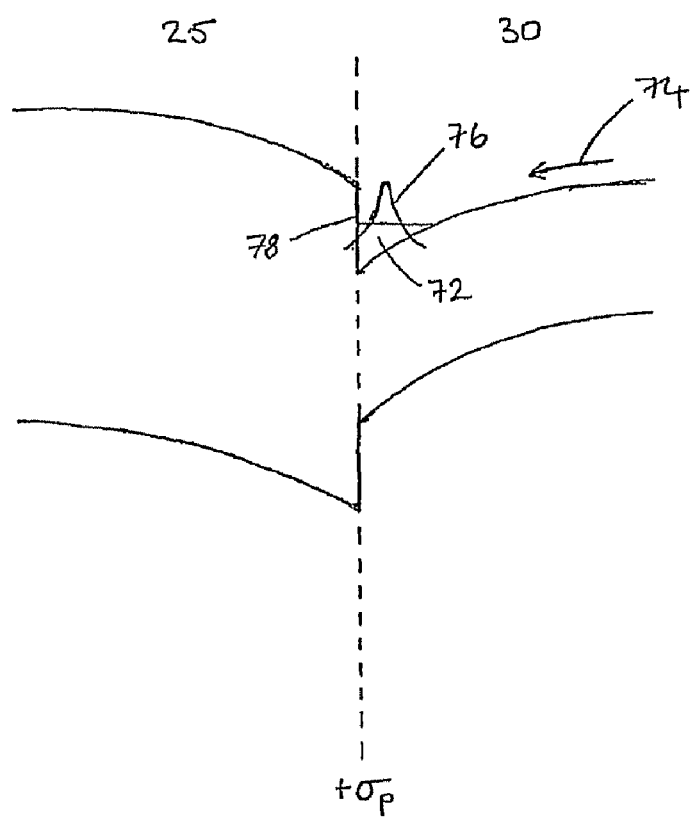
FIG. 4 shows an energy band diagram for the interface between the polar and diamond layers shown in FIG. 3.

An energy band diagram for the interface between the polar layer and the intrinsic diamond channel is shown in FIG. 4.

The n-type doped layer 45 acts as a source of electrons and the electric field resulting from the polarisation sheet charge $+\sigma_P$ attracts the electrons from the n-type doped layer 45 towards the interface with the polar layer 25, along path 74 as shown in FIG. 4. The discontinuity 78 in the conduction band minimum between the diamond layer 10 and the polar layer 25 acts as a potential barrier which prevents transfer of electrons from the diamond layer into the polar layer. The electrons 72 are trapped in an approximately triangular potential well in the intrinsic diamond channel close to the interface with the polar layer. This results in a highly confined 2DEG in region 70 of the intrinsic diamond channel close to the interface.

The square modulus of the electron wave function $|\phi(z)|^2$ 76 is a maximum in the diamond layer, rather than at the interface. Therefore, transport of electrons occurs in the high purity and high crystalline quality intrinsic diamond channel rather than along the doped region or the polar layer or along the interface itself, either of which would lead to significant carrier scattering effects.

Figure 5:
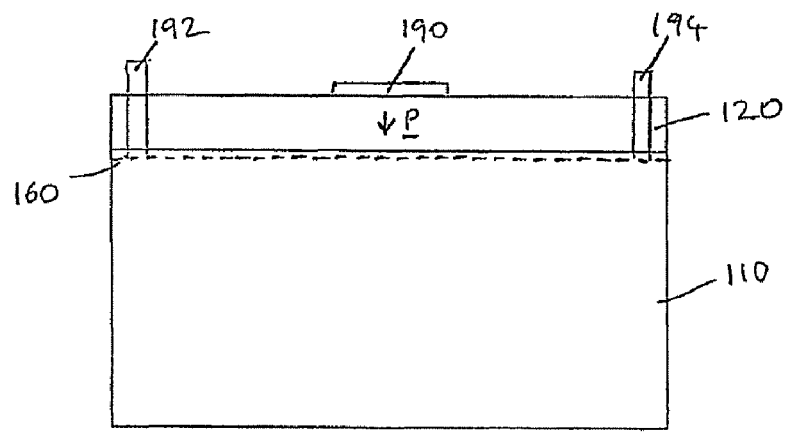
FIG. 5 shows a third embodiment of a PEFET according to the present invention.

A third embodiment of the present invention is shown in FIG. 5. An n-type doped polar layer 120 is disposed on an intrinsic diamond layer 110 so that its polarisation vector points substantially towards the interface between the polar layer 120 and the intrinsic diamond layer 110. The n-type doped layer does not have to be doped uniformly; it may just contain a doped layer within it. The n-type doped polar layer is either epitaxially grown or bonded onto the intrinsic diamond layer. The n-type doped polar layer 120 has a band gap greater than that of the intrinsic diamond layer 110. The intrinsic diamond layer has a band gap, $E_g$, of 5.47 eV. The n-type doped polar layer may comprise a Si doped Al-polar AlN layer. The thickness of the doped polar layer is believed to be limited by the need for the transistor to function in pinch-off mode. A gate contact 190 is arranged on the polar layer 120 and a source 192 and a drain 194 are arranged to contact the intrinsic diamond layer 110.

With an Al-polar Si doped AlN layer, the discontinuity in polarisation between the intrinsic diamond layer 110 and the doped polar layer 120 creates a positive polarisation-induced sheet charge $+\sigma_P$ at the interface between the two layers. This sheet charge leads to a significant strength electric field.

Figure 6:
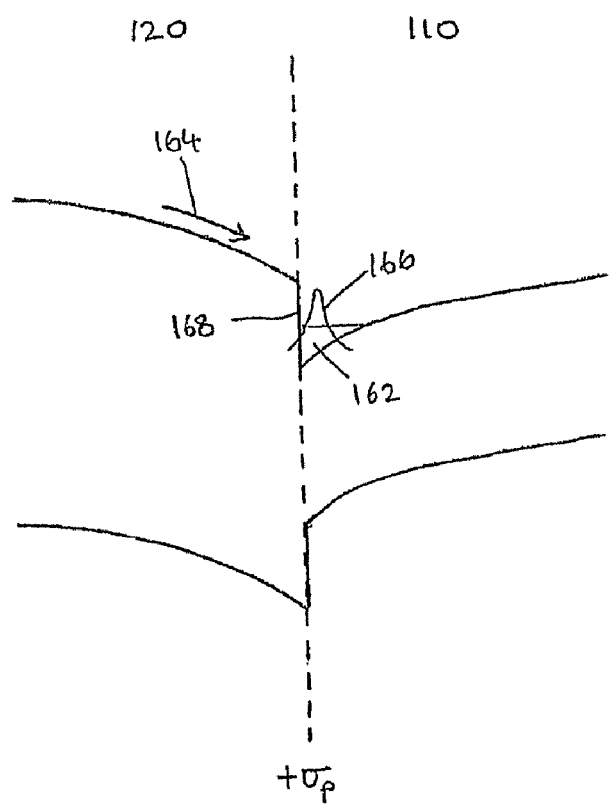
FIG. 6 shows an energy level band for the interface between the polar and diamond layers shown in FIG. 5.

An energy band diagram for the interface between the doped polar layer and the intrinsic diamond channel is shown in FIG. 6.

The n-type doped polar layer 120 acts as a source of electrons and the electric field resulting from the polarisation sheet charge $+\sigma_P$ results in the transfer, which may be by tunnelling, of electrons from the doped polar layer 120 through the interface and into the intrinsic diamond layer 110, along path 164 as shown in FIG. 6. The discontinuity 168 in the conduction band minima between the diamond layer 110 and the polar layer 120 acts as a potential barrier which contains the electrons in the intrinsic diamond layer. The electrons 162 are trapped in a triangular potential well in the intrinsic diamond channel close to the interface with the polar layer. This results in a highly confined 2DEG in region 160 of the intrinsic diamond layer 110 close to the interface.

The square modulus of the electron wave function $|\phi(z)|^2$ 166 is a maximum in the diamond layer, rather than at the interface. Therefore, transport of electrons occurs in the high purity and high crystalline quality intrinsic diamond channel rather than along the doped region or the polar layer or along the interface itself, either of which would lead to significant carrier scattering effects.

Figure 7:
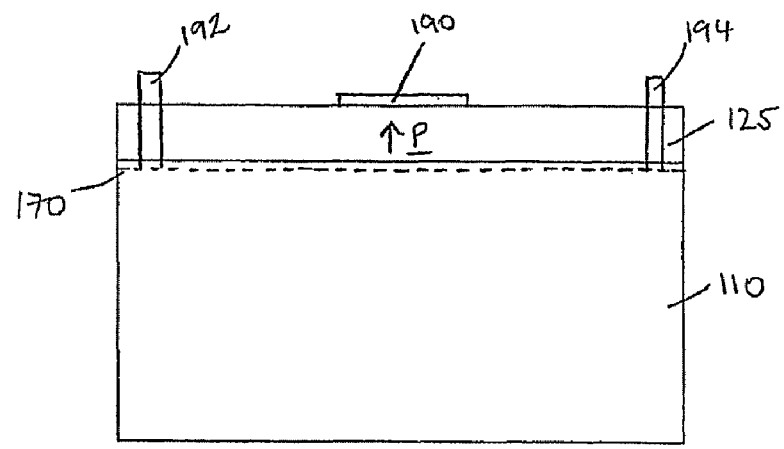
FIG. 7 shows a fourth embodiment of a PEFET according to the present invention.

A fourth embodiment of the present invention is shown in FIG. 7. A p-type doped polar layer 125 is disposed on an intrinsic diamond layer 110 so that its polarisation vector points substantially away from the interface between the polar layer 125 and the intrinsic diamond layer 110. The p-type doped layer does not have to be doped uniformly; it may just contain a doped layer within it. The p-type doped polar layer is either epitaxially grown or bonded onto the intrinsic diamond layer. The p-type doped polar layer 125 has a band gap greater than that of the intrinsic diamond layer 110. The intrinsic diamond layer has a band gap, $E_g$, of 5.47 eV. The p-type doped polar layer may comprise an Mg-doped N-polar AlN layer. The thickness of the doped polar layer is believed to be limited by the need for the transistor to function in pinch-off mode. A gate contact 190 is arranged on the polar layer 125 and a source 192 and a drain 194 are arranged to contact the intrinsic diamond layer 110.

With a p-type doped N-polar AlN layer, the discontinuity in polarisation between the intrinsic diamond layer 110 and the doped polar layer 125 creates a negative polarisation-induced sheet charge $-\sigma_P$ at the interface between the two layers. This sheet charge leads to a significant strength electric field.

Figure 8:
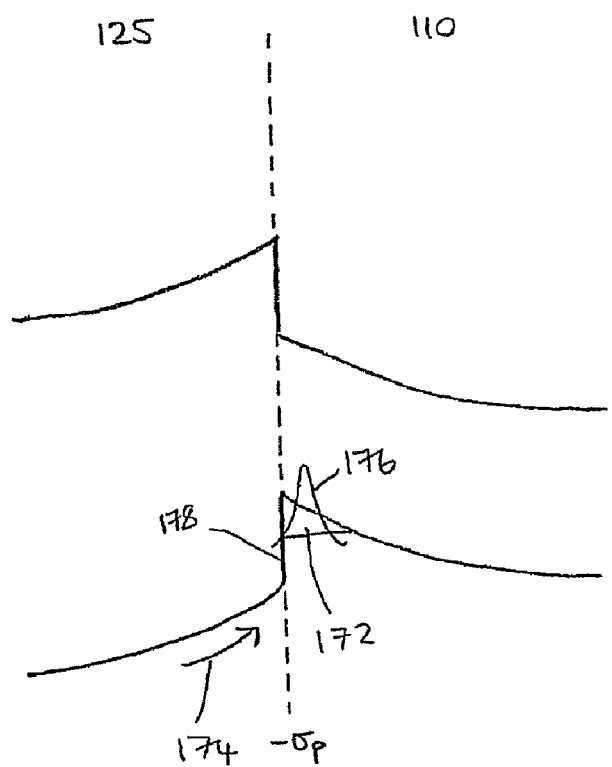
FIG. 8 shows an energy band diagram for the interface between the polar and diamond layers shown in FIG. 7.

An energy band diagram for the interface between the doped polar layer and the intrinsic diamond channel is shown in FIG. 8.

The p-type doped polar layer 125 acts as a source of holes and the electric field resulting from the polarisation sheet charge $-\sigma_P$ results in the transfer of holes from the doped polar layer 125 through the interface and into the intrinsic diamond layer 110, along path 174 as shown in FIG. 8. The discontinuity 178 in the valence band maxima between the diamond layer 110 and the polar layer 125 acts as a potential barrier which contains the holes 172 in the intrinsic diamond layer. The holes 172 are trapped in a triangular potential well in the intrinsic diamond channel close to the interface with the polar layer. This results in a highly confined 2DHG in region 170 of the intrinsic diamond layer 110 close to the interface.

The square modulus of the hole wave function $|\phi(z)|^2$ 176 is a maximum in the diamond layer, rather than at the interface. Therefore, transport of holes occurs in the high purity and high crystalline quality intrinsic diamond channel rather than along the doped region or the polar layer or along the interface itself, either of which would lead to significant carrier scattering effects.

Figure 9:
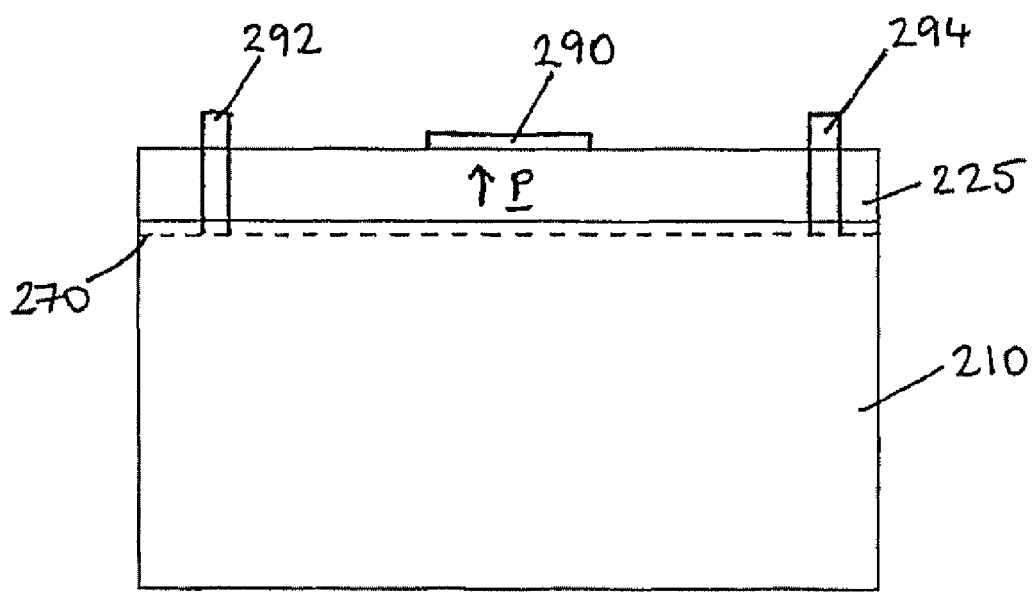
FIG. 9 shows a fifth embodiment of a PEFET according to the present invention.

A fifth embodiment of the present invention is shown in FIG. 9. A polar layer 225 is disposed on an intrinsic diamond layer 210 so that its polarisation vector points substantially away from the interface between the polar layer 225 and the intrinsic diamond layer 210. The polar layer 225 has a band gap greater than that of the intrinsic diamond layer 210. The intrinsic diamond layer has a band gap, $E_g$, of 5.47 eV. The polar layer may comprise an N-polar AlN layer. The thickness of the polar layer is believed to be limited by the need for the transistor to function in pinch-off mode. A gate contact 290 is arranged on the polar layer 225 and a source 292 and a drain 294 are arranged to contact the intrinsic diamond layer 210.

With an N-polar AlN layer, the discontinuity in polarisation between the intrinsic diamond layer 210 and the polar layer 225 creates a negative polarisation-induced sheet charge $-\sigma_P$ at the interface between the two layers. This sheet charge leads to a significant strength electric field which may causes the valence band maximum to intersect the Fermi level ($E_F$). Holes would be generated near the interface which act as carriers.

Figure 10:
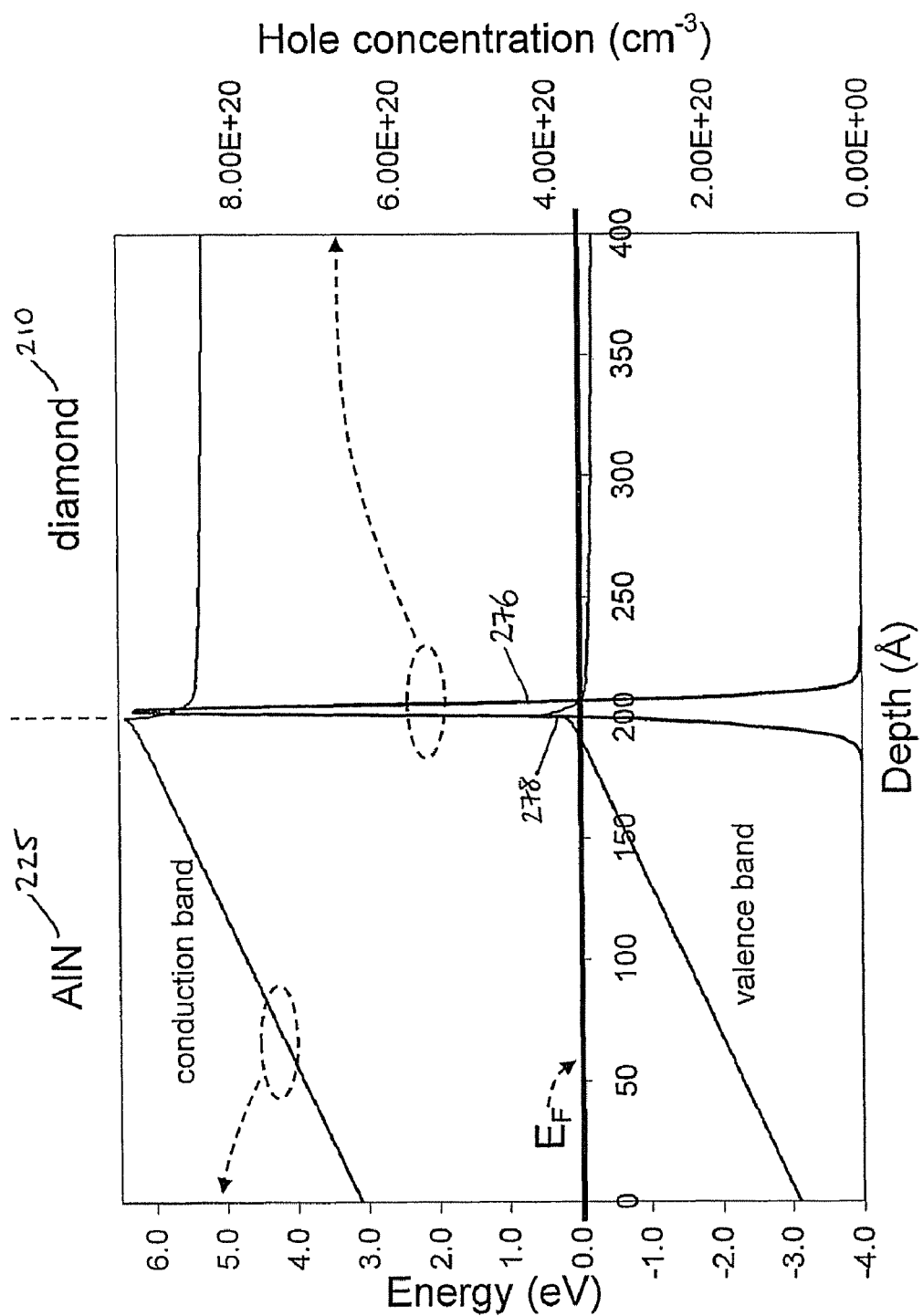
FIG. 10 shows an energy band diagram for the interface between the polar and diamond layers shown in FIG. 9.

An energy band diagram for the interface between the polar MN layer and the intrinsic diamond layer is shown in FIG. 10.

The electric field resulting from the polarisation sheet charge $-\sigma_P$ results in the generation of holes in the diamond layer 210 near the interface as shown in FIG. 10. The discontinuity 278 in the valence band maxima between the diamond layer 210 and the polar layer 225 acts as a potential barrier which contains the holes in the intrinsic diamond layer. The holes are trapped in a triangular potential well in the intrinsic diamond channel close to the interface with the polar layer. This results in a highly confined 2DHG in region 270 of the intrinsic diamond layer 210 close to the interface.

The square modulus of the hole wave function $|\phi(z)|^2$ 276 is a maximum in the diamond layer, rather than at the interface. Therefore, transport of holes occurs in the high purity and high crystalline quality intrinsic diamond channel rather than along the polar layer or along the interface itself, either of which would lead to significant carrier scattering effects.

It will of course be understood that the present invention has been described above purely by way of example, and that modifications of detail can be made within the scope of the invention as defined by the claims.

The invention claimed is:

1. An electronic field effect device comprising:
   an interface between two materials, wherein the interface is formed by:
     a first diamond layer, at least a first surface of which comprises crystalline intrinsic diamond, and
     a second layer disposed on the first surface of the first layer, wherein the second layer is polar and includes a doped region comprising a p-type layer, the second layer being arranged so that a component of its polarization vector P points away from the interface;
   wherein there is a discontinuity in polarization between the first layer and the second layer; and
   there is a band offset between the first layer and the second layer, in the band in which the dominant charge carriers are present, such that the dominant charge carriers are confined to a planar region within the first layer and in close proximity to the interface by the combined effects of a polarization induced sheet charge and an electric field provided by the discontinuity in polarization between the first layer and the second layer, and the band offset.

2. The electronic field-effect device of claim 1 wherein the second layer comprises a pyroelectric layer.

3. The electronic field-effect device of claim 1 wherein the diamond layer comprises synthetic diamond formed by chemical vapor deposition.

4. The field effect device of claim 1 wherein the first surface of the first diamond layer is formed by deposition.

5. The field effect device of claim 4 wherein the first surface of the first diamond layer is prepared from a processed surface with an $R_q$ of less than 10 nm by growing a further thin layer using a CVD process, wherein the thickness of this layer, grown onto the previously prepared surface, is less than 20 μm.

6. The field effect device of claim 1 wherein the first surface of the first diamond layer has a dislocation density determined using the method of X-ray topography of less than 400 $cm^{-2}$ over an area greater than 0.014 $cm^2$.

7. A method of forming an electronic field-effect device comprising:

forming an interface between a first layer and a second layer by:
   providing a first diamond layer, at least a first surface of which comprises crystalline intrinsic diamond having a root-mean-square roughness, $R_q$, of less than 10 nm; and
   providing a second layer, wherein the second layer is polar and includes a doped region comprising a p-type layer, the second layer being arranged so that a component of its polarization vector P points away from the interface, and the second layer is arranged on the first surface of the first layer, wherein:
there is a discontinuity in polarization between the first layer and the second layer; and
there is a band offset between the first layer and the second layer, in the band in which the dominant charge carriers are present, such that the dominant charge carriers are confined to a planar region within the first layer and in close proximity to the interface by the combined effects of a polarization induced sheet charge and an electric field provided by the discontinuity in polarization between the first layer and the second layer, and the band offset.

8. The method of claim 7 wherein the step of providing a first layer comprises forming a diamond layer by chemical vapor deposition (CVD).

* * * * *